(12) United States Patent
Neumann et al.

(10) Patent No.: US 6,756,513 B2
(45) Date of Patent: Jun. 29, 2004

(54) PROCESS FOR PREPARING MONOCHLORINATED HYDROCARBONS HAVING A HIGH ISOMERIC PURITY

(75) Inventors: Manfred Neumann, Marl (DE); Clemens Osterholt, Dorsten (DE)

(73) Assignee: Degussa AG, Duesseldorf (DE)

( * ) Notice: Subject to any disclaimer, the term of this patent is extended or adjusted under 35 U.S.C. 154(b) by 15 days.

(21) Appl. No.: 10/219,289

(22) Filed: Aug. 16, 2002

(65) Prior Publication Data

US 2003/0065232 A1 Apr. 3, 2003

(30) Foreign Application Priority Data

Aug. 16, 2001 (DE) .......................................... 101 40 268

(51) Int. Cl.$^7$ ......................... C07C 17/02; C07C 17/04; C07C 17/08; C07C 17/10; C07C 21/00; C07C 23/00; C07C 25/00
(52) U.S. Cl. ...................... 570/247; 570/190; 570/191; 570/192; 570/246
(58) Field of Search ................................ 570/190, 191, 570/192, 246, 247

(56) References Cited

U.S. PATENT DOCUMENTS 4,233,444 A * 11/1980 Doonan et al. ............. 544/192

OTHER PUBLICATIONS

Stanley R. Sandler, "Cyanuric Chloride. A Novel Laboratory Hydrochlorinating Reagent for Alcohols," *J. Org. Chem.*, vol. 35, No. 11, 1979, p. 3967–3968. XP–002226615.
Lidia De Luca et al, "An Efficient Route to Alkyl Chlorides from Alcohols Using the Complex TCT/DMF," *Organic Letters*, vol. 4, No. 4, 553–555, 2002. XP–002226616.

* cited by examiner

*Primary Examiner*—Elvis O. Price
(74) *Attorney, Agent, or Firm*—Oblon, Spivak, McClelland, Maier & Neustadt, P.C.

(57) ABSTRACT

Monochlorinated hydrocarbons of high isomeric purity are prepared by a process, which comprises:
reacting a monoalcohol having an alkyl radical having from 3 to 20 carbon atoms with cyanuric chloride; and
purifying the resulting monochlorinated hydrocarbon by distillation after separation of salts and washing the monochlorinated hydrocarbon with alkali.

The invention relates to a process for preparing monochlorinated hydrocarbons which contain an alkyl radical having from 3 to 20 carbon atoms and have a high isomeric purity by reacting a monoalcohol having a hydrocarbon radical containing an alkyl radical having from 3 to 20 carbon atoms to which additional cycloaliphatic radicals, aryl radicals, aralkyl radicals and alkylaryl radicals may be bound with cyanuric chloride, separating off salts, washing the reaction mixture with alkali and purifying the resulting monochlorinated hydrocarbons by distillation.

20 Claims, No Drawings

PROCESS FOR PREPARING MONOCHLORINATED HYDROCARBONS HAVING A HIGH ISOMERIC PURITY

BACKGROUND OF THE INVENTION

1. Field Of The Invention

The present invention relates to a process for preparing monochlorinated hydrocarbons which bear an alkyl radical having from 3 to 20 carbon atoms to which the chlorine atom is bound. In the process, appropriate alcohols are reacted with cyanuric chloride and the reaction mixture is subsequently worked-up.

2. Discussion Of The Background

Monochlorinated hydrocarbons such as alkyl chlorides are, inter alia, valuable as intermediates for the preparation of crop protection agents and pharmaceutical products. They are therefore often required in a high isomeric purity.

The preparation of monochlorinated hydrocarbons such as alkyl chlorides generally starts from olefins or alcohols.

Methods of preparing isomerically pure alkyl chlorides are known and described in the literature. S. R. Sandler, J. Org. Chem. 35, 3967 (1970), describes the conversion of primary, secondary and tertiary alcohols into alkyl chloride compounds by reacting the alcohols with an excess of cyanuric chloride under anhydrous conditions. Furthermore, on page 3968 of the text, the reaction of 2-pentanol with cyanuric chloride, zinc chloride/hydrogen chloride, thionyl chloride/pyridine and with hydrogen chloride is described. Isomerically pure 2-chloro-pentane is obtained in a yield of 48% in the reaction with thionyl chloride/pyridine and in a yield of 57% in the reaction with cyanuric chloride alone.

Disadvantages of these processes are, in particular, a) that a residual amount of cyanuric chloride remains in the crude monochlorinated hydrocarbon after the solids (cyanuric chloride, cyanuric acid and derivatives) have been separated and there is considerable sublimate formation in the work-up by distillation, b) that very long reaction times are sometimes required when the number of carbon atoms in the hydrocarbon portion of the molecule increases, and c) that large amounts of toxic pyridine have to be handled and pyridine hydrochloride is formed in large amounts when using thionyl chloride/pyridine. A need continues to exist for an improved method of producing isomerically pure monochlorinated hydrocarbons in high space time yield.

SUMMARY OF THE INVENTION

Accordingly, one object of the present invention is to provide a simple process by means of which isomerically pure monochlorinated hydrocarbons, which contain an alkyl radical having from 3 to 20 carbon atoms to which the chlorine atom is bound and to which additional hydrocarbon radicals may be bound, can be prepared in high space-time yields.

Briefly, this object and other objects of the present invention as hereinafter will become more readily apparent can be attained by reacting a monoalcohol with cyanuric chloride with or without addition of a phase transfer catalyst (PTC) and then purifying the resulting mono-chlorinated hydrocarbon by distillation after mechanical removal of salts and washing of the product with alkali.

DETAILED DESCRIPTION OF THE PREFERRED EMBODIMENTS

The reaction of the invention can be illustrated schematically by means of the scheme below.

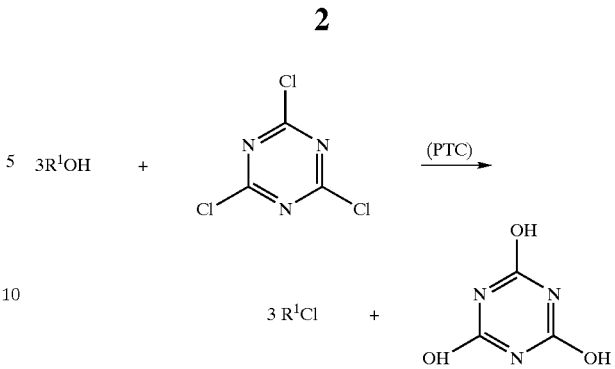

$R^1$ is a hydrocarbon radical which is a primary, secondary or tertiary alkyl radical having from 3 to 20 carbon atoms. The alkyl radicals may be unbranched or branched, saturated or unsaturated. From 0 to 3 cycloaliphatic radicals having from 3 to 8 carbon atoms, for example, cyclopentyl or cyclohexyl radicals, from 0 to 3 alkyl-substituted or unsubstituted aryl radicals having from 6 to 16 carbon atoms, for example, phenyl, naphthyl, tolyl or xylyl radicals, or from 0 to 3 aralkyl radicals having from 7 to 16 carbon atoms, for example, benzyl or phenylethyl radicals, optionally are bonded to the alkyl radical. Preferred alcohol reactants are secondary aliphatic alcohols having from 5 to 16, in particular from 6 to 16, preferably from 5 to 14, in particular from 6 to 14, particularly preferably from 5 to 12, and most preferably from 6 to 12, carbon atoms.

The molar ratio of monoalcohol:cyanuric chloride in the reaction ranges from 1:3 to 4:1, preferably from 3:1.5 to 3:2.

The temperature of the reaction ranges from 10° C. to 150° C. preferably from 30° C. to 100° C., below the boiling point of the monochlorinated hydrocarbon formed. the interests of simplicity, atmospheric pressure is preferred.

The reaction can also be conducted in the presence of a solvent having a boiling point above the boiling point of the monochlorinated hydrocarbon formed. In this case, the reaction of the alcohol with the cyanuric chloride can also be conducted at a temperature above the boiling point of the monochlorinated hydrocarbon formed.

The reaction can be conducted in the absence of a phase transfer catalyst. However, it has surprisingly been found that the addition of a small amount of a phase transfer catalyst enables the reaction time to be significantly shortened. For example, a reaction time of 36 hours is required to achieve virtually complete reaction of 6-undecanol with cyanuric chloride at a reaction temperature of 100° C. (Example 1). Addition of a phase transfer catalyst under otherwise identical reaction conditions makes a reaction time of only 8 hours sufficient (Example 2).

Examples of suitable phase transfer catalysts include quaternary ammonium salts and quaternary phosphonium salts, e.g. tetraalkylammonium salts, advantageously having $C_1$–$C_8$-alkyl radicals, in particular $C_1$–$C_4$-alkyl radicals, or aralkyl radicals having from 7 to 16 carbon atoms in the aralkyl radical, for example the benzyl radical, or alkylaryl radicals having from 7 to 16 carbon atoms in the alkylaryl radical, for example tolyl or ethylphenyl radicals. The anionic component of the salts can be, for example, halides, hydrogensulfates or sulfates. Preference is given to halides, in particular chlorides. Representative embodiments of the phase transfer catalysts, in particular, are tetrabutylammonium chloride, benzyltriethylammonium chloride and methyltrioctyl-ammonium chloride. Crown ethers, in particular 18-crown-6, can also be used as phase transfer catalysts.

The phase transfer catalysts are advantageously used in an amount which ranges from 0.001 to 0.2 times, preferably from 0.005 to 0.1 times, particularly preferably from 0.01 to 0.05 times, the weight of the monoalcohol used (from 0.1 to 20% by weight based on the monoalcohol).

It is also possible to use mixtures of phase transfer catalysts.

Another advantage of the process of the invention resides in the work-up of the reaction product. The solid material that is produced by the reaction, which is predominantly a mixture of cyanuric chloride, cyanuric acid and derivatives thereof, can be mechanically separated, for example, by filtration, centrifugation or decantation, and, if appropriate, washing with a solvent, for example, cyclohexane or olefins. Washing leaves a residual amount of dissolved cyanuric chloride in the filtrate, centrifugate or decantate. The solvent used for washing is preferably the olefin formed as a by-product in the process. Prior to the work-up by distillation, the filtrate is subjected to washing with alkali. Sodium hydroxide or potassium hydroxide is preferably used for this purpose. The alkali concentration of the preferred aqueous washing liquors ranges from 1 to 60% by weight, preferably from 15 to 30% by weight. The amount of washing liquor employed ranges from 2 to 80%, preferably from 6 to 12%, based on the crude product mixture.

The monochlorinated hydrocarbon is subsequently purified by distillation, preferably under reduced pressure.

The aqueous phase obtained in the washing step (extraction) can be passed to a specific work-up for wastewater containing cyanuric chloride.

The preparation of the monochlorinated hydrocarbons can be conducted batchwise or continuously.

Having generally described this invention, a further understanding can be obtained by reference to certain specific examples which are provided herein for purposes of illustration only and are not intended to be limiting unless otherwise specified.

EXAMPLES

Example 1

Preparation of 6-chloroundecane in the Absence of a Phase Transfer Catalyst

A 250 g (1.445 mol) amount of 6-undecanol is placed in a 1 liter stirred flask provided with a glass blade stirrer and a reflux condenser. The temperature of the reaction is set to 100° C. on an oil bath and 144.4 g (0.783 mol) of cyanuric chloride is metered in over a period of 2 hours. After a total reaction time of 36 hours at 100° C., a conversion of about 99% of the 6-undecanol is achieved.

The two-phase reaction mixture (solid/liquid) is filtered and the solid is washed with cyclohexane (50 g). The liquid reaction product and the cyclohexane washings are combined (289.3 g) and extracted with 67 g of 8% strength by weight sodium hydroxide solution.

Product composition after the treatment with sodium hydroxide (calculated on a cyclohexane-free basis):

| | |
|---|---|
| undecenes | 20% |
| 6-chloroundecane | 74% |
| isomeric chloroundecanes | <0.02% |
| 6-undecanol | 1% |

-continued

| | |
|---|---|
| diundecyl ether | 4% |
| unknown balance | 1% |

In the work-up by distillation, the target product 6-chloroundecane is obtained in a purity of >99%. The yield of 6-chloroundecane is 55% of theory, based on the 6-undecanol used.

Example 2

Preparation of 6-chloroundecane in the Presence of a Phase Transfer Catalyst

The procedure of Example 1 is repeated, but the difference being that 2.4 g of tetrabutylammonium chloride is initially placed in the reaction flask together with the 6-undecanol (250 g). After a total running time of only 8 hours at 100° C., the 6-undecanol conversion is 99%.

The proportion of isomeric chloroundecanes rises slightly to 0.4%. The crude product composition otherwise corresponds to that in Example 1.

Example 3

Preparation of 3-chlorooctane

Using a procedure analogous to that of Example 1, 81 g (0.522 mol) of 3-octanol is reacted with 62.1 g (0.337 mol) of cyanuric chloride over a period of 9 hours at a reaction temperature of 70° C. The liquid reaction phase after extraction with sodium hydroxide has the following composition:

| | |
|---|---|
| octenes | 23% |
| 3-chlorooctane | 69% |
| isomeric octyl chlorides | <0.5% |
| 3-octanol | 1.5% |
| dioctyl ether | 5% |
| unknown balance | <1% |

Example 4

Preparation of 2-chloropentane

Using a procedure analogous to that of Example 1, 100 g (1.134 mol) of 2-pentanol is reacted with 113 g (0.613 mol) of cyanuric chloride over a period of 5 hours at a reaction temperature of 70° C.

The liquid reaction phase after extraction with sodium hydroxide has the following composition:

| | |
|---|---|
| 2-methyl-1-butene | 12% |
| 2-chloropentane | 76% |
| isomeric chloropentanes | — |
| 2,2'-oxybispentane | 11% |
| 2-pentanol | <0.3% |
| unknown balance | <1% |

Example 5

Preparation of 1-chloro-1-phenylethane

Using a procedure analogous to that of Example 1, 100 g (0.82 mol) of 1-phenylethane-1-ol is reacted with 97.6 g (0.529 mol) of cyanuric chloride over a period of 14 hours at a reaction temperature of 90° C. After phase separation, treatment with sodium hydroxide and purification by distillation, 1-chloro-1-phenylethane having a purity of>99% and containing<0.3% of isomeric alkyl chlorides is obtained.

The disclosure of German priority application 10140268.6 filed Aug. 16, 2001 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by Letters Patent is:

1. A process, which comprises:
    reacting a monoalcohol having an alkyl radical having from 3 to 20 carbon atoms with cyanuric chloride in the presence of a phase transfer catalyst; and
    purifying the resulting monochlorinated hydrocarbon by distillation after separation of salts and washing the monochlorinated hydrocarbon with alkali, thereby preparing at least one monochlorinated hydrocarbon having a high isomeric purity.

2. The process as claimed in claim 1, wherein the alkyl radical of the monoalcohol containing from 3 to 20 carbon atoms is unbranched, branched, saturated or unsaturated, and the alcoholic group is bound to a primary, secondary or tertiary carbon atom of the alcohol and the alkyl radical optionally bears from 0 to 3 cycloaliphatic radicals having from 3 to 8 carbon atoms, from 0 to 3 alkyl-substituted or unsubstituted aryl radicals having from 6 to 16 carbon atoms or from 0 to 3 arylalkyl radicals having from 7 to 16 carbon atoms.

3. The process as claimed in claim 2, wherein the cycloaliphatic radical is cyclopentyl or cyclohexyl, the aryl radical is phenyl, naphthyl, tolyl or xylyl and the arylalkyl radical is phenylethyl or benzyl.

4. The process as claimed in claim 1, wherein the monoalcohol is a secondary aliphatic alcohol and contains from 5 to 16 carbon atoms.

5. The process as claimed in claim 4, wherein the monoalcohol is a secondary aliphatic alcohol and contains from 6 to 16 carbon atoms.

6. The process as claimed in claim 1, wherein the molar ratio of alcohol:cyanuric chloride reactants ranges from 1:3 to 4:1.

7. The process as claimed in claim 6, wherein the molar ratio of alcohol:cyanuric chloride reactants ranges from 3:1.5 to 3:2.

8. The process as claimed in claim 1, wherein the reaction is conducted at a temperature ranging from 10° C. to 150° C. below the boiling point of the monochlorinated hydrocarbon formed.

9. The process as claimed in claim 8, wherein the reaction temperature ranges from 30° C. to 100° C. below the boiling point of the monochlorinated hydrocarbon formed.

10. The process as claimed in claim 1, wherein the reaction is conducted in a solvent having a boiling point above the boiling point of the monochlorinated hydrocarbon that is formed during the reaction.

11. The process as claimed in claim 1, wherein a phase transfer catalyst is present in the reaction medium in a concentration ranging from 0.1 to 20% by weight based on the amount of the monoalcohol.

12. The process as claimed in claim 11, wherein the amount of said phase transfer catalyst ranges from 0.5 to 10% by weight based on the amount of the monoalcohol.

13. The process as claimed in claim 11, wherein the phase transfer catalyst is a quaternary ammonium salt, a quaternary phosphonium salt, a crown ether or a mixture of these compounds.

14. The process as claimed in claim 13, wherein the phase transfer catalyst is a tetraalkylammonium halide.

15. The process as claimed in claim 1, which is conducted in a batchwise fashion.

16. The process as claimed in claim 1, which is conducted continuously.

17. The process as claimed in claim 1, wherein the alkali of the alkali wash is sodium hydroxide or potassium hydroxide.

18. The process as claimed in claim 1, wherein the washing with alkali is carried out with an aqueous solution having an alkali concentration of 1 to 60% by weight.

19. The process as claimed in claim 18, wherein the alkali concentration ranges from 15 to 30% by weight.

20. The process as claimed in claim 1, wherein the reaction is conducted at an absolute pressure ranging from 0.5 to 10 bar.

* * * * *